(12) United States Patent
Liu et al.

(10) Patent No.: US 9,315,671 B2
(45) Date of Patent: Apr. 19, 2016

(54) BAY-ANNULATED INDIGO (BAI) AS AN EXCELLENT ELECTRON ACCEPTING BUILDING BLOCK FOR HIGH PERFORMANCE ORGANIC SEMICONDUCTORS

(71) Applicants: Yi Liu, Fremont, CA (US); Bo He, Albany, CA (US); Andrew Pun, Folsom, CA (US)

(72) Inventors: Yi Liu, Fremont, CA (US); Bo He, Albany, CA (US); Andrew Pun, Folsom, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/942,775

(22) Filed: Nov. 16, 2015

(65) Prior Publication Data

US 2016/0075878 A1 Mar. 17, 2016

Related U.S. Application Data

(62) Division of application No. 14/687,059, filed on Apr. 15, 2015, now Pat. No. 9,196,846.

(60) Provisional application No. 61/981,043, filed on Apr. 17, 2014.

(51) Int. Cl.
*C09K 3/00* (2006.01)
*C07D 471/22* (2006.01)
*C09B 7/02* (2006.01)
*H01L 51/00* (2006.01)
*H01L 51/05* (2006.01)

(52) U.S. Cl.
CPC .............. *C09B 7/02* (2013.01); *H01L 51/0068* (2013.01); *H01L 51/0072* (2013.01); *H01L 51/0074* (2013.01); *H01L 51/0094* (2013.01); *H01L 51/0558* (2013.01)

(58) Field of Classification Search
USPC ........................................ 252/182.11; 546/41
See application file for complete search history.

(56) References Cited

PUBLICATIONS

Fallon, K.J. et al.: A nature-inspired conjugated polymer for high performance transistors and solar cells. Macromolecules, vol. 48, pp. 5148-5154, 2015.*

\* cited by examiner

*Primary Examiner* — Charanjit Aulakh
(74) *Attorney, Agent, or Firm* — Lawrence Berkeley National Laboratory

(57) ABSTRACT

A novel electron acceptor based on bay-annulated indigo (BAI) was synthesized and used for the preparation of a series of high performance donor-acceptor small molecules and polymers. The resulting materials possess low-lying LUMO energy level and small HOMO-LUMO gaps, while their films exhibited high crystallinity upon thermal treatment, commensurate with high field effect mobilities and ambipolar transfer characteristics.

1 Claim, 13 Drawing Sheets

7,14-di(thiophen-2-yl)diindolo[3,2,1-*de*:3',2',1'-*ij*][1,5]naphthyridine-6,13-dione

T-BAI-T(1)

7,14-bis(5-bromothiophen-2-yl)diindolo[3,2,1-*de*:3',2',1'-*ij*][1,5]naphthyridine-6,13-dione

2

7,14-bis(5'-hexyl-[2,2'-bithiophen]-5-yl)diindolo[3,2,1-*de*:3',2',1'-*ij*][1,5]naphthyridine-6,13-dione

2T-BAI-2TC6(4)

2T-BAI-2TC12(6)

7,14-bis(3'-dodecyl-[2,2'-bithiophen]-5-yl)diindolo[3,2,1-*de*:3',2',1'-*ij*][1,5]naphthyridine-6,13-dione 7,14-bis(5'-bromo-3'-dodecyl-[2,2'-bithiophen]-5-yl)diindolo[3,2,1-*de*:3',2',1'-*ij*][1,5]naphthyridine-6,13-dione

7

Poly-5,5'-(7,14-bis(3'-dodecyl-[2,2'-bithiophen]-5-yl)diindolo[3,2,1-de:3',2',1'-ij][1,5]naphthyridine-6,13-dione)-2,6-(4,8-bis((2-octyldodecyl)oxy)benzo[1,2-b:4,5-b']dithiophene)

Poly-5,5'-(7,14-bis(3'-dodecyl-[2,2'-bithiophen]-5-yl)diindolo[3,2,1-de:3',2',1'-ij][1,5]naphthyridine-6,13-dione)-2,7-(9-(heptadecan-9-yl)-9H-carbazole)

BAY-ANNULATED INDIGO (BAI) AS AN EXCELLENT ELECTRON ACCEPTING BUILDING BLOCK FOR HIGH PERFORMANCE ORGANIC SEMICONDUCTORS

CROSS REFERENCE TO RELATED APPLICATIONS

This application is a divisional application of U.S. application Ser. No. 14/687,059 filed Apr. 15, 2015 now U.S. Pat. No. 9,196,846, which claims priority to U.S. Provisional Application Ser. No. 61/981,043 filed Apr. 17, 2014, which application is incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

BACKGROUND OF THE INVENTION

1. Field of the Invention

The present invention relates to the field of organic semiconductor and organic photovoltaics.

2. Related Art

A major trend in the development of high performance organic semiconductors is reflected by the recent burst of research efforts on low bandgap small molecules and polymers. As a common structural feature of the majority of such materials, alternating electron-rich (donor) and electron-deficient (acceptor) units are linked along an electroactive backbone. Their highly modular synthesis protocols, which rely on potent metal catalyzed cross-coupling reactions between electron donors and acceptors, essentially provide access to an unlimited number of functional materials for applications in organic field effect transistors (OFETs) and organic photovoltaics (OPVs). Along the lines of materials discovery, the search for efficient electron donor and acceptor units is among the most critical steps for better control of key materials parameters, such as electronic energy levels, optical bandgaps and absorptivity, and thin film morphology.

FIG. 1a illustrates structures of several commonly used electron deficient building blocks. Over the years, several popular electron acceptors have become the workhorses in the development of high performance low bandgap materials, such as benzothiadiazole (BTD), diketopyrrolopyrrole (DPP), isoindigo (iI), benzobisthiadiazole (BBT), and those based on rylene diimides. Small molecules and polymers incorporating these units have displayed impressive power conversion efficiency in organic photovoltaics (OPVs) and remarkable charge transport mobilities in organic field effect transistors (OFETs).

Some of these acceptors, such as DPP and iI, are based on industrial pigments, which add extra value in terms of materials stability. The centrosymmetric ketopyrrole cores of DPP and iI are, however, not readily available from naturally occurring pigments and have to be built through a few synthetic steps. On the other hand indigo, as one of the oldest known dyes, possesses a similarly appealing symmetric ketopyrrole structure and is a low cost pigment material (several US dollars per kilogram) that can be obtained from natural sources or synthetically. Despite the fact that native indigo and its derivatives have received more attention for their high performance in ambipolar FET transistors, their direct use as electronic materials is restricted, largely due to their limited solubility. Functionalization of indigo would both increase its solubility and modify its electronic properties. FIG. 1b illustrates different motifs of functionalizing Indigo. The bonds in the hatched rectangle highlight the conjugation pathway in the BAI core.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

Figure 1:
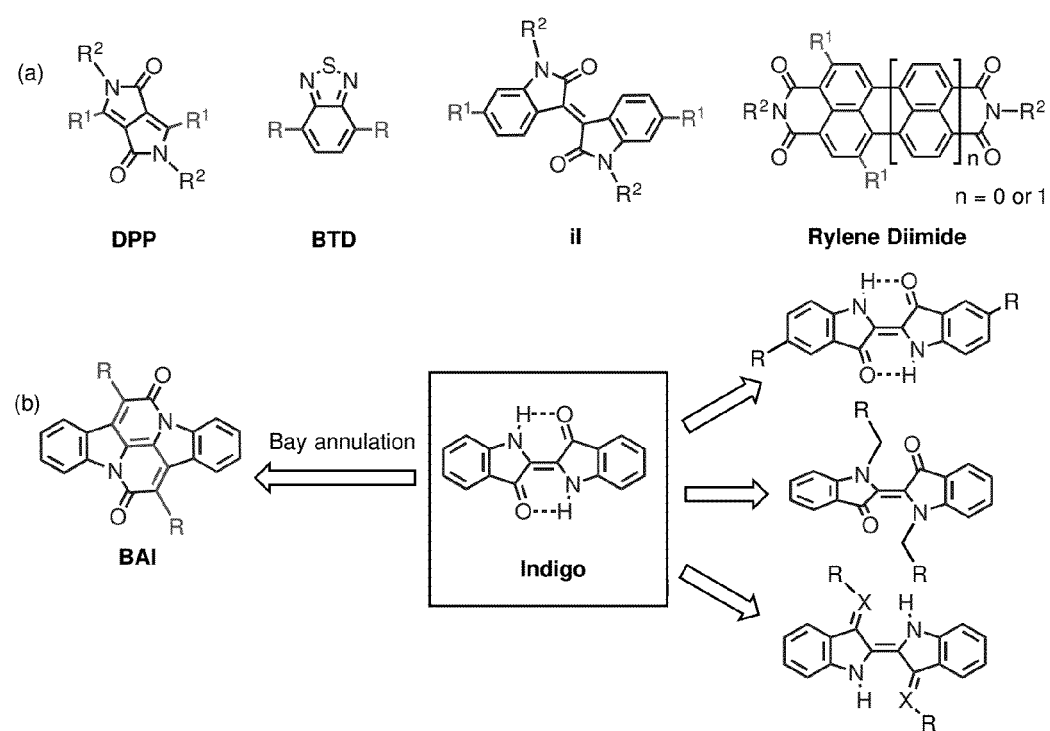
FIG. 1 illustrates (a) structures of several commonly used electron deficient building blocks. (b) Illustration of different motifs of functionalizing Indigo. The bonds in hatched rectangle highlight the conjugation pathway in the BAI core.

Indigo has a trans-planar molecular structure due to strong intramolecular hydrogen bonding between the two 3-oxindole units that are centrosymmetrically connected by a double bond. Functionalization of indigo can be realized on three positions (see FIG. 1b)—one on the two end benzene rings, and the others on the nitrogen or carbonyl groups at the bay positions of the oxindole units. The disadvantage of the former motif is that the conjugation does not extend over the central double bond and thus the π electron resonance is localized within each oxindole unit. On the other hand, derivatization on the bay positions introduces steric groups that twist the two oxindole units out of plane, unless these units are fixed into a coplanar geometry where both carbonyl groups and N atoms are incorporated into an annulated diketopiperidinopiperidine structure (See FIG. 1b). In addition to reinforced planarity, this annulation also facilitates effective conjugation across the bay—as the part highlighted in hatched rectangle in FIG. 1b—to the substituents. This bay annulated indigo (BAI) constitutes the core of the dye Cibalackrot that contains two phenyl substituents, however both synthetic details and its use as electroactive units remain underexplored thus are worth further exploration. Indeed the synthetic chemistry on directly functionalizing indigo is remarkably scarce in spite of the recent reports on ketone- or N-derivatized indigo. Here we report the synthesis of BAI and its use as a new potent electron acceptor. Both experimental and theoretical modeling reveals that they have low lying LUMO energies and narrow optical bandgaps. Moreover, this electron acceptor is compatible with Stille and Suzuki coupling reaction conditions. Novel donor-acceptor-donor (DAD) triads and donor-acceptor polymers are prepared in this way, which have shown promising electronic and optical properties.

Figure 2:
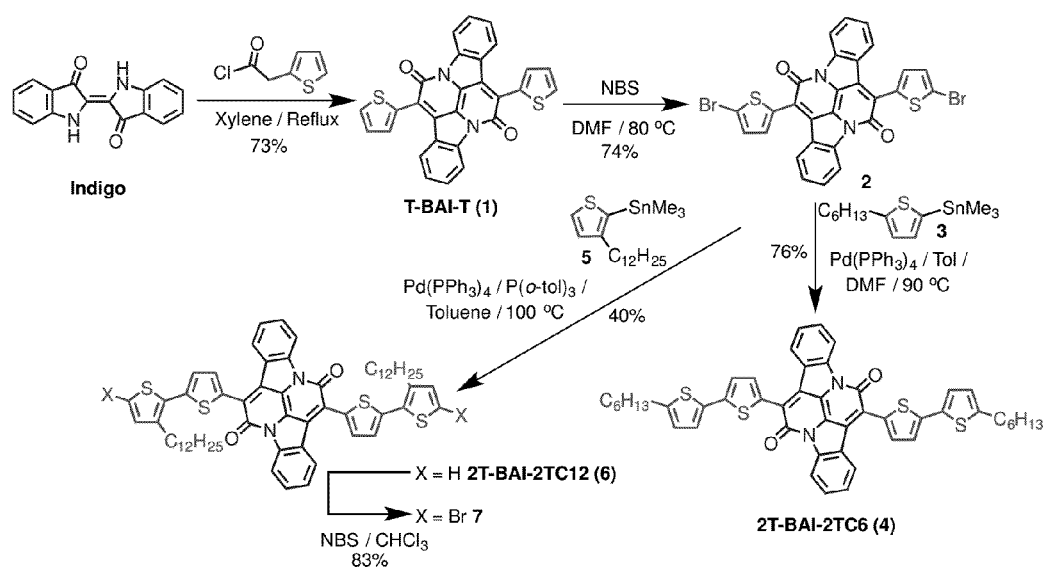
FIG. 2 illustrates Synthesis of BAI-based small molecules.
Figure 3:
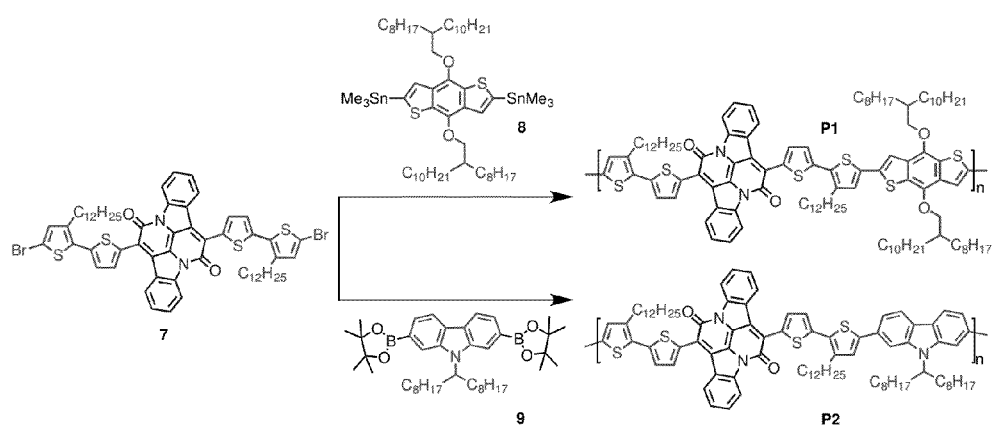
FIG. 3 illustrates synthesis of polymers P1 and P2.

FIG. 2 illustrates the synthesis of BAI-based small molecules. Our research targeted the synthesis of thiopheneflanked BAI through direct double annulation of the indigo core. Heating a mixture of indigo and 2-thienylacetyl chloride in xylene under reflux produced the T-BAI-T (1) composition in an approximate 73% yield. This double annulation presumably undergoes sequential amidation and intramolecular aldol condensation steps to give the desired product in potentially one step. Bromination of composition (1) using N-bromosuccinimide (NBS) in DMF yields a dibromide composition (2) in an approximate 74% yield, which undergoes Stille coupling with either composition (3) or composition (5) to give the D-A-D type molecules 2T-BAI-2TC6 (4) composition and 2T-BAI-2TC12 (6) composition. Further bromination of composition (6) gives rise to the corresponding dibromide composition (7) (See FIG. 3), which polymerizes with either the benzodithiophene stannane (8) or carbazole boronic ester (9) to yield D-A polymers (P1) or (P2) in 86% and 82% yields, respectively (See FIG. 3 the synthesis of polymers (P1) and (P2)).

Figure 10:
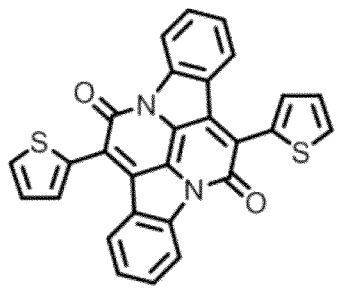
FIG. 10 illustrates a T-BAI-T composition (1), a dibromide composition (2), and a 2T-BAI-2TC6 composition (4).
Figure 10:
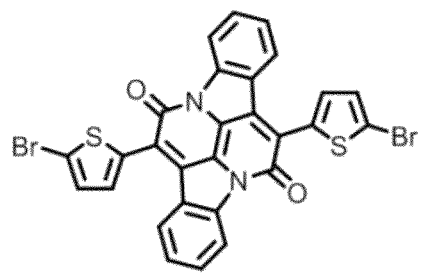
Figure 10:
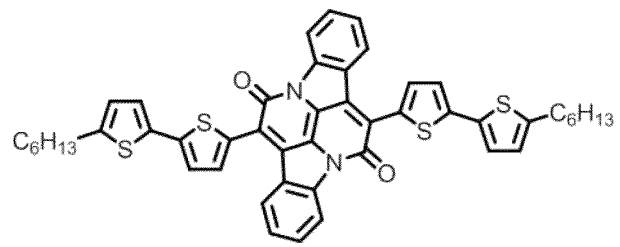
Figure 11:
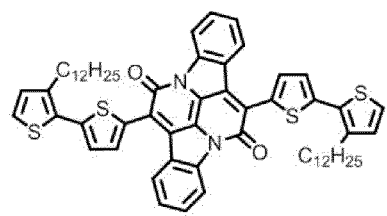
FIG. 11 illustrates a 2T-BAI-2TC12 composition (6) and a corresponding dibromide composition (7).
Figure 11:
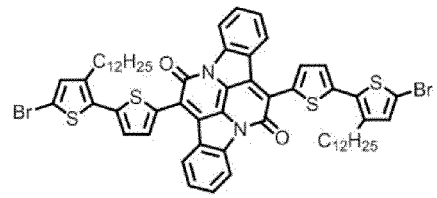
Figure 12:
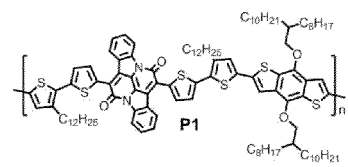
FIG. 12 illustrates D-A polymers (P1) and (P2).
Figure 12:
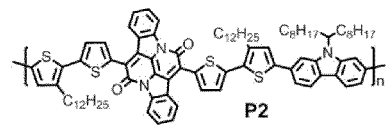

The T-BAI-T composition (1), the dibromide composition (2), and the 2T-BAI-2TC6 composition (4) are illustrated in FIG. 10. The 2T-BAI-2TC12 composition (6) and the corresponding dibromide composition (7) are illustrated in FIG. 11. The D-A polymers (P1) and (P2) are illustrated in FIG. 12.

Figure 13:
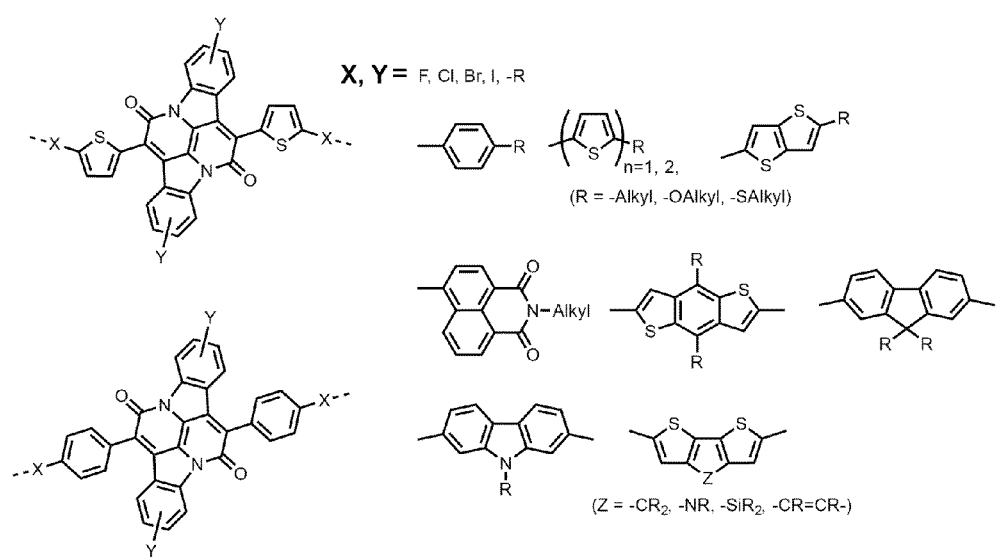
FIG. 13 illustrates a generalized scheme of a chemical library of BAIs. All structures are based on the genus of BAI core with different variations on the -X and -Y groups.

FIG. 13 illustrates a generalized scheme of a chemical library of BAIs. All structures are based on the genus of BAI core with different variations on the -X and -Y groups.

Figure 4:
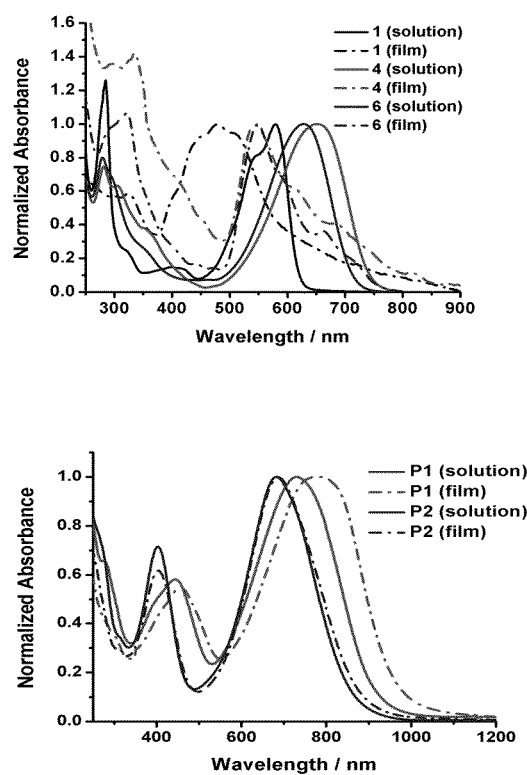
FIG. 4 illustrates UV-Vis absorption spectra of the BAI (a) small molecules and (b) polymers in solution ($CHCl_3$) and in thin films.

Optical absorption spectra of the BAI derivatives are evaluated both in dilute solutions and as thin films (see FIG. 4), and the relevant data are summarized in Table 1. The absorption spectrum of T-BAI-T (1) displays two absorption bands at 530 nm and 580 nm, respectively. The former band can be attributed to the π-π* transition and the latter attributable to an intramolecular charge transfer, both being characteristic of donor-acceptor systems. The maximum absorption shows a 20-40 nm blue shift with respect to the parent Indigo, consistent with indigoids losing intramolecular hydrogen bonding and the "H-chromophore" characteristics. The absorption maximum of 2T-BAI-2TC6 (4) undergoes bathochromic shift to 650 nm, and to 670 nm in the case of 2T-BAI-2TC12 (6), together with the loss of the fine peak splitting feature. The red shift clearly suggests extended conjugation due to the extra thiophene units, and the difference between (4) and (6) is attributable to steric induced nonplanarity of the bithiophene units by the 3-alkyl substitution in (6). Interestingly, the electronic spectra of thin films of these compounds display hypochromic shift of these transitions, which indicate H-aggregation in the solid state. For donor-acceptor polymer P1 and P2, they absorb in the near IR region with an absorption maximum at around 700 and 750 nm in solution, and display characteristic bathochromic shift to 720 nm and 830 nm in the thin films. The optical bandgaps of these materials are estimated from the onset of absorption of both solution and thin film spectra and listed in Table 1. The strong absorption in the near IR region clearly indicated the electron withdrawing character of the BAI unit.

TABLE 1

Summary of optical and electrochemical parameters.

| | UV-vis | | | | | | Cyclic voltammetry (film) | | |
| --- | --- | --- | --- | --- | --- | --- | --- | --- | --- |
| | solution | | | film | | | | | |
| Cpd | $\lambda_{max}$ (nm) | $\lambda_{onset}$ (nm) | $E_g^{opt}$ (eV) | $\lambda_{max}$ (nm) | $\lambda_{onset}$ (nm) | $E_g^{opt}$ (eV) | HOMO (eV) | LUMO (eV) | $E_g^{ele}$ (eV) |
| 1 | 579 | 620 | 1.98 | 477 | 800 | 1.55 | −5.38 | −3.53 | 1.85 |
| 4 | 652 | 740 | 1.67 | 545 | 823 | 1.51 | −5.15 | −3.62 | 1.53 |
| 6 | 629 | 712 | 1.74 | 549 | 760 | 1.63 | −5.20 | −3.61 | 1.59 |
| P1 | 737 | 950 | 1.31 | 779 | 1000 | 1.24 | −4.91 | −3.63 | 1.28 |
| P2 | 682 | 880 | 1.41 | 699 | 904 | 1.37 | −5.03 | −3.65 | 1.38 |

Figure 5:
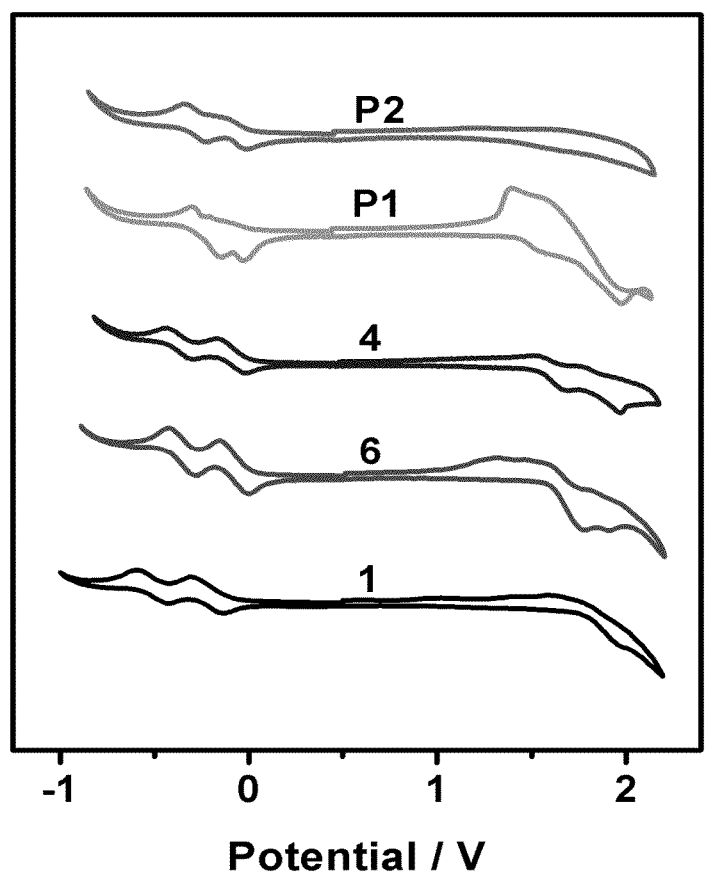
FIG. 5 illustrates cyclic voltagram of the BAI derivatives. The potential is referenced to the $F_c/F_c^+$ redox couple.

The electrochemical properties of BAI compounds were investigated using cyclic voltammetry (FIG. 5 and Table 1). Two reversible one-electron reduction processes were observed for all the BAI—based small molecules. The energy levels of the lowest unoccupied molecular orbitals (LUMOs) of BAI-containing compounds were estimated to be around −3.6 eV, indicative of BAI's excellent electron accepting characteristics. The electrochemical bandgaps match well with the optical bandgaps (see Table 1), from which the highest occupied molecular orbitals (HOMOs) could be derived.

Figure 6:
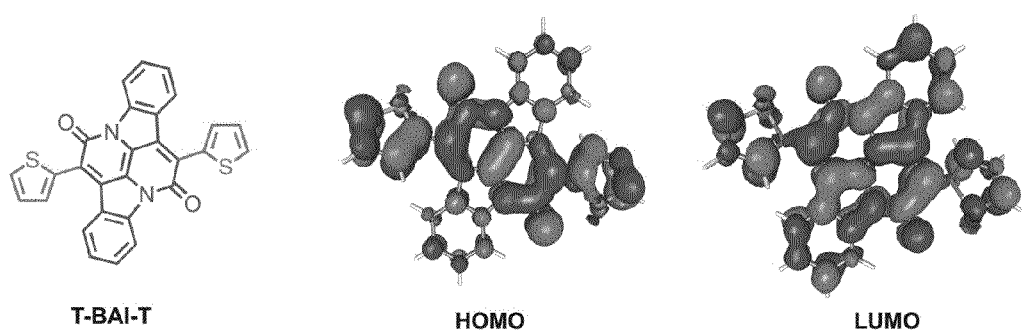
FIG. 6 illustrates isodensity surfaces (0.03 e/bohr$^3$) of the HOMO and LUMO of the T-BAI-T molecule.

Density functional theory (DFT) calculations on the nature of the molecular orbitals and the frontier orbital energies (FOEs) are carried out on T-BAI-T and compared against several other popular electron acceptors. Both geometry optimization and FOEs are calculated at the B3LYP/6-31G* level. As depicted in FIG. 6, the BAI unit in T-BAI-T adopts a planar structure, with the HOMO spread over the diketopiperidopiperidine unit and extending to the conjugated thiophene units but much less so to the two orthogonally arranged benzene rings in the BAI core. On the other hand, the LUMO is highly delocalized over the aromatic surface of T-BAI-T, including the two annulated benzene rings. The extensive delocalization might account for the low-lying LUMO character of the BAI core, while the HOMO is dominated by the conjugation along the orthogonal direction that involves the diketopiperidopiperidine and the thiophene units.

Figure 7:
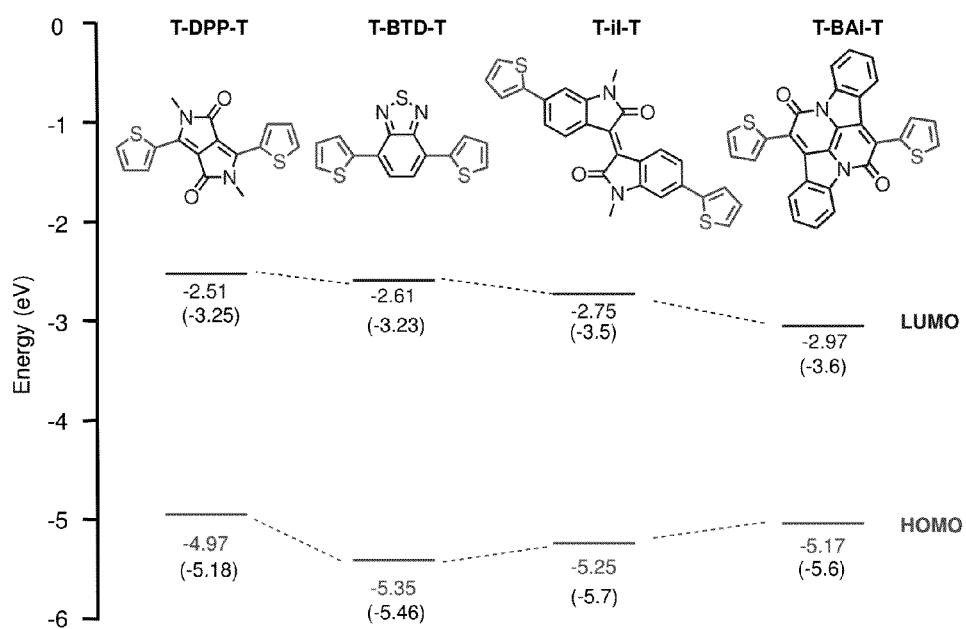
FIG. 7 illustrates a correlation diagram of frontier orbital energies of four representative acceptor units. R=Me in the case of T-DPP-T and T-iI-T.

The calculated FOEs of the T-BAI-T were compared against T-DPP-T, T-BTD-T, and T-iI-T, all of which are in a similar donor-acceptor-donor fashion and differ mainly by the center acceptor units. Methyl groups are used for N-substituents in the cases of T-DPP-T and T-iI-T for simplicity. The predicted order of the LUMO energies agrees well with the experimental results. It is also worth noting that our calculations of the FOEs of the known acceptors reproduce the reported theoretical values. As can be seen from FIG. 7, T-BAI-T has the lowest LUMO energy, which is about 0.24 eV lower than the second lowest iI acceptor. On the other hand, the HOMO is only slightly higher than iI but significantly lower the DPP acceptor. The calculated bandgap is 2.2 eV, which agrees well with the experimental optical and electrochemical bandgap (2.0 eV).

Figure 8:
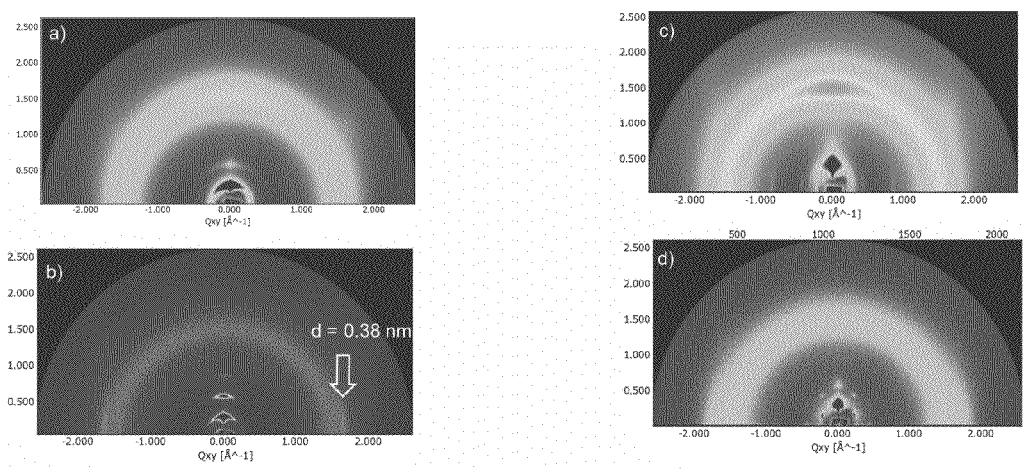
FIG. 8 illustrates GIWAXS of spin casted thin films of a) and b) P1 and c) and d) P2. a) and c) as cast films, b) and d) annealed films.
Figure 9:
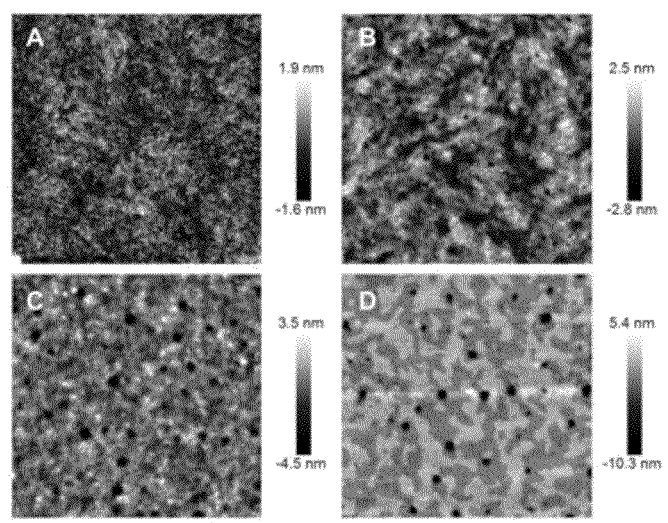
FIG. 9 illustrates AFM images of a) and b) P1 and c) and d) P2. a) and c) as cast films, b) and d) annealed films.

Grazing incident wide-angle X-ray scattering (GIWAXS) measurements were conducted to probe the molecular packing within the spin-casted films of P1 and P2. For the as-cast thin film of P1, a strong (100) scattering peak is observed, indicating some preferential orientation of the polymer chain on the substrate. Once annealed to above 250° C., higher order out-of-plane (h00) scattering peaks appeared (FIG. 8), corresponding to a well-ordered lamellar structure with an edge-on orientation of the polymer chains on the substrate and an inter-lamellar distance of 2.15 nm. This orientation is further confirmed by the appearance of the in-plane (010) scattering peak at d=3.83 Å, which is attributable to interchain π-π stacking. On the other hand, the GIWAXS of the as-cast P2 films revealed parallel brag rods as well as a broad (100) π-stacking peak, indicating the formation of vertically aligned lamellar structures. Once annealed to above 150° C., the brag rods transformed into defined brag spots, revealing a change of molecular packing from lamellae into hexagons. The difference in molecular packing suggests that the interchain interactions differ significantly in P1 and P2. Atomic force microscopic (AFM) images of both unannealed polymer films indicate (FIG. 9) the formation of fiber-like intercalating networks. Both the crystallite domain size and the roughness increase slightly after annealing due to molecular reorganization and changes of molecular packing within the film.

The charge carrier transport properties of these polymers were evaluated in bottom-gate/top-contact (BG/TC) device configurations. The BG/TC devices were fabricated by first spin casting the polymer solution (chloroform or THF) on an octadecyltrisilane-treated silicon substrate (with a 300-nm-thick thermally grown oxide layer), followed by thermal deposition of Au source and drain electrodes. All devices were fabricated in glove boxes, transferred to an enclosed chamber in a Lakeshore probe station, and tested under vacuum. The as-cast BG/TC devices of P1 show nearly unipolar p-type transport characteristics (FIG. 8), with a hole mobility of $3.8 \times 10^{-3}$ $cm^2V^{-1}S^-$. Annealing P1 at 250° C. for 5 min resulted in ambipolar device behavior with a nearly 5 times enhanced hole mobilities and an electron mobility of $7.8 \times 10^{-3}$ $cm^2V^{-1}S^{-1}$. In comparison, the as-cast BG/TC devices of P2 were ambipolar (FIG. 8), with a hole and electron mobility of $3.2 \times 10^{-3}$ and $1.0 \times 10^{-4}$ $cm^2V^{-1}S^{-1}$. Annealing at 150° C. for 30 min enhances the hole mobility by three times, and for the electron mobility, a more than two order enhancement was observed (additive effect to be included).

The ambipolar behavior is a strong indication of the electron accepting nature of the BAI unit. The lamellar or hexagonal packing revealed by GIWAXS attest to strong interchain interactions and well-behaved self-assembly processes in the thin films. As been demonstrated by Pei and others, further modification of the polymers by altering the side chain structures is effective to enhance molecular order and packing within the thin film. Thus we envision that higher efficiency carrier transport can be realized with further side chain engineering.

In summary, we have designed and synthesized a new electron acceptor unit that is based on readily available indigo dye. The synthesis of BAI is realized by a one-pot reaction that involves sequential amidation and aldol condensation steps to give a new annulated diketopiperidinopiperidine core. As shown by both experiment and theory, BAI derivatives inheriting some structure features of the parent indigo have low-lying LUMO energy levels and narrow bandgaps. The derivatization on the indigo ensures extension of the π-conjugation without disturbing the planarity of indigo, resulting in novel electron acceptors that are stronger than some other imide-based acceptors such as isoindigo and DPP derivatives. The versatility of the BAI acceptor has been demonstrated by its facile incorporation into donor-acceptor-donor triads and low bandgap donor-acceptor polymers through conventional metal-catalyzed cross-coupling reactions. These materials exhibit tunable optoelectronic properties, thermally responsive self-assembly behavior, as well as ambipolar charge transporting characteristics. On account of the easy access to cheap starting material and the straightforward chemistry, this BAI acceptor holds great promise as a versatile electron deficient building block for the discovery of new series of high performance optoelectronic materials.

Materials and Methods

Reagents were purchased from Aldrich or synthesized as described. Dry solvents were collected from a solvent purification system. Thin-layer chromatography (TLC) was carried out using aluminum sheets, precoated with silica gel 60F (Merck 5554). The plates were inspected by UV-light. Proton and carbon nuclear magnetic resonance spectra ($^1$H-NMR and $^{13}$C-NMR) spectra were recorded on a Bruker Avance500 II, using locking to the deuterated solvent and using tetramethylsilane as an internal standard. All chemical shifts are quoted using the δ scale, and all coupling constants (J) are expressed in Hertz (Hz). Matrix-assisted laser desorption ionization (MALDI) mass spectra were measured on 4800 MALDI TOF/TOF analyzer from Applied Biosystems. Thermal properties were recorded by using Q5000 Thermal Gravity Analysis (TGA) and TA Q200 Differential Scanning calorimeters (DSC). Film Thickness was measured using a Dektak 150 profilometer. Cyclic voltammetry was performed using a 273A potentiostat (Princeton Applied Research), wherein glassy carbon, platinum and a silver wire act as the working electrode, the counter electrode and the pseudo-reference electrode, respectively. Samples were prepared in $CHCl_3$ solution with tetrabutylammonium hexafluorophosphate (0.1 M) as the electrolyte at a scan rate of 100 mV s$^{-1}$, using ferrocene/ferronium ($F_c/F_c^+$) redox couple as an internal standard. The HOMO and LUMO levels of compounds are calculated from the difference between the first oxidation potential ($E_{oxi}$) or reduction potential ($E_{red}$) of the compounds and the oxidation potential of ferrocene ($E_{HOMO}$=−(4.8-$E_{oxi}$) eV, $E_{LUMO}$=−(4.8-$E_{red}$) eV). GIWAXS was acquired at Stanford Synchrotron Radiation Lightsource (SSRL) and at Beamline 7.3.3, Advanced Light Source, Lawrence Berkeley National Laboratory.

UV-Vis-NIR spectra were recorded using a Cary 5000 UV-Vis-NIR spectrometer. The electrical characteristics of the transistors were measured using Lakeshore Probe Station model of CPX-HF and Aligent 4155C Semiconductor Parameter Analyzer at room temperature under vacuum ($10^{-3}$ Torr). A Thermal-Oriel 300W solar simulator provided an AM 1.5G solar illumination at 100 mW cm$^{-2}$ for OPV device testing. A Keithley 236 source-measure unit was used to measure current density-voltage (J-V) curves.

FET Device Fabrication

Transistors were fabricated in the bottom-gate/top-contact configuration on highly doped n-type (100) Si substrates (<0.02Ω cm) with 300-nm-thick thermally grown silicon dioxide as the dielectric layer. The Si substrates (1.6×1.4 cm$^2$) were successively ultrasonicated in soap water, water, acetone and isopropyl alcohol before being dried in an oven at 130° C. for 1 hour. Octadecyltrichlorosilane was deposited by submerging the substrates in a 0.1 vol % solution of octadecyltrichlorosilane in toluene in a closed jar for 8 hours. The substrates were subsequently washed with toluene and dried in an oven at 130° C. for at least 1 hour before further use. The capacitance per unit area of the gate dielectric layer (SiO$_2$, 300 nm) was $C_i$=11.5 nF cm$^{-2}$. The polymer solutions were filtered through poly(tetrafluoroethylene) (PTFE, 0.45 μm) filters prior to film deposition. All the organic thin films were spuncast onto the OTS modified Si substrates from chloroform solutions (5 mg mL$^{-1}$) at a rotation rate of 3000 rpm for 30 s, followed by annealing at certain temperatures as noted. Sample annealing was carried out for 5 mins, and followed by slow cooling to room temperature over 30 minutes. Finally, gold source/drain electrodes (50 nm thick) were evaporated on top through a metal mask (9 pixels/chip) with channel width and length of 3 mm and 100 μm, respectively. The average mobility was obtained from a minimum of 3-9 pixels from 1-3 different chips. Scratching the SiO$_2$ dielectric layer off n-doped Si substrates provided gate electrodes. The thermal annealing was performed on a hotplate in a glove box filled with N$_2$. All the FET measurements were performed under vacuum ($10^{-3}$ Torr) at room temperature.

Material Synthesis

FIG. 10 illustrates the overall synthetic scheme of BAI derivatives. Indigo, 2-thiopheneacetyl chloride and composition 9 were purchased from Sigma-Aldrich and used without purification. Compositions 3, 5 and 8 were synthesized according to literature. Compositions 1, 2, 4, 6, 7, P1 and P2 were synthesized as described in the following synthetic procedures.

Composition 1: To a refluxing xylene (50 mL) suspension of indigo (1.00 g, 3.81 mmol, 1.0 eq), a solution of 2-thiopheneacetyl chloride (1.88 mL, 15.2 mmol, 4.0 eq) in xylene (5 mL) was added dropwise over 30 minutes. The half and double annulated indigo derivatives were observed as purple and red spots on the TLC plate respectively. The reaction was stopped when the purple spot completely disappeared by TLC. After cooling to room temperature, the precipitate was filtered and rinsed with THF, yielding the title product 1 (1.6 g, 73%) as a red solid. $^1$H NMR (CDCl$_3$, 500 MHz): δ=8.57 (d, J=8.0 Hz, 2H), 8.16 (d, J=7.8 Hz, 2H), 7.73 (dd, J=3.6 Hz, J=0.9 Hz, 2H), 7.69 (dd, J=5.1 Hz, J=0.9 Hz, 2H), 7.59 (t, J=7.8 Hz, 2H), 7.31 (t, J=7.5 Hz, 2H), 7.28 (dd, J=5.1 Hz, J=1.3 Hz, 2H). $^{13}$C NMR (CDCl$_3$, 125 MHz): δ=158.87, 144.14, 134.66, 132.29, 130.59, 130.23, 130.10, 126.47, 126.28, 125.77, 125.12, 124.85, 122.28, 117.88. MS MALDI-TOF m/z 474.22 (M$^+$, Calcd 474.05).

Composition 2: To a suspension of composition 1 (1.00 g, 2.11 mmol) in CHCl$_3$ (100 mL) was added NBS (787 mg, 4.43 mmol, 2.1 eq) in portions. After overnight stiffing at room temperature, water was added to quench the reaction. The suspension was filtered and rinsed with water, acetone and CHCl$_3$, giving the title product 2 (1.11 g, 83%) as a purple solid. $^1$H NMR (CDCl$_3$, 500 MHz): δ=8.57 (d, J=7.9 Hz, 2H), 8.22 (d, J=7.8 Hz, 2H), 7.62 (t, J=7.8 Hz, 2H), 7.55 (d, J=3.9 Hz, 2H), 7.35 (t, J=7.3 Hz, 2H), 7.23 (d, J=3.9 Hz, 2H). The acquisition of a $^{13}$C NMR spectrum with good signal-to-noise ratio was unsatisfactory due to limited solubility. MS MALDI-TOF m/z 630.07 (M$^+$, Calcd 629.87).

Composition 4: Under N$_2$ atmosphere, a deoxygenated mixture of 2 (300 mg, 474 μmol, 1.0 eq), (5-hexylthiophen-2-yl)trimethylstannane (361 mg, 1.09 mmol, 2.3 eq), and Pd(PPh$_3$)$_4$ (27.4 mg, 23.7 μmol, 0.05 eq) in toluene (12 mL) and DMF (3 mL) was stirred overnight at 90° C. After cooling to room temperature, the precipitate was collected by filtration and rinsed with hexane. Recrystallization of the precipitate from toluene gave the title product 4 (290 mg, 76%) as a purple solid. $^1$H NMR (CDCl$_3$, 500 MHz): δ=8.63 (d, J=8.1 Hz, 2H), 8.33 (d, J=7.8 Hz, 2H), 7.73 (d, J=3.8 Hz, 2H), 7.61 (t, J=8.0 Hz, 2H), 7.35 (t, J=7.5 Hz, 2H), 7.27 (d, J=3.8 Hz, 2H), 7.18 (d, J=3.5 Hz, 2H), 6.75 (d, J=3.5 Hz, 2H), 2.84 (t, J=7.5 Hz, 4H), 1.72 (m, 4H), 1.41 (m, 4H), 1.33 (m, 8H), 0.91 (t, J=7.0 Hz, 6H). M.p. 277° C. The acquisition of a $^{13}$C NMR spectrum with good signal-to-noise ratio was unsatisfactory due to limited solubility. MS MALDI-TOF m/z 806.34 (M$^+$, Calcd 806.21).

Composition 6: Under N$_2$ atmosphere, a deoxygenated mixture of 2 (500 mg, 790 μmol, 1.0 eq), (3-dodecylthiophen-2-yl)trimethylstannane (788 mg, 1.90 mmol, 2.4 eq), Pd(PPh$_3$)$_4$ (21.7 mg, 23.7 μmol, 0.03 eq) and P(o-tol)$_3$ (28.9 mg, 95 μmol, 0.12 eq) in toluene (40 mL) was stirred overnight at 100° C. After cooling to room temperature, the reaction mixture was condensed under reduced pressure and subjected to silica gel chromatography column with hexane/CHCl$_3$ (1:1) as the eluent. The blue fraction collected from the column was concentrated and recrystallized from cyclohexane to give the title product 6 (310 mg, 40%) as a purple solid. M.p. 202° C. $^1$H NMR (CDCl$_3$, 500 MHz): δ=8.62 (d, J=8.1 Hz, 2H), 8.32 (d, J=8.0 Hz, 2H), 7.76 (d, J=3.8 Hz, 2H), 7.59 (t, J=7.5 Hz, 2H), 7.35 (t, J=8.0 Hz, 2H), 7.29 (d, J=3.8 Hz, 2H), 7.24 (d, J=5.2 Hz, 2H), 6.98 (d, J=5.2 Hz, 2H), 2.89 (t, J=7.8 Hz, 4H), 1.70 (m, 4H), 1.40 (m, 4H), 1.22 (m, 16H), 0.84 (t, J=6.9 Hz, 6H). $^{13}$C NMR (CDCl$_3$, 500 MHz): δ=158.76, 143.90, 141.77, 140.42, 134.44, 132.06, 130.80, 130.57, 130.32, 129.43, 126.3, 125.9, 125.04, 124.52, 124.49, 121.97, 117.92, 31.93, 30.65, 29.71, 29.67, 29.66, 29.6, 29.55, 29.38, 22.70, 14.14. MS MALDI-TOF m/z 974.46 (M$^+$, Calcd 974.40).

Composition 7: NBS (153.3 mg, 0.86 mmol, 2.1 eq) was added to an ice-bath cooled solution of 6 (400 mg, 0.41 mmol, 1.0 eq) in CHCl$_3$. The reaction was allowed to run at room temperature overnight. The solution was washed with water and dried with brine and MgSO$_4$. The residue from filtration and vacuum evaporation was subjected to silica gel chromatography column with CHCl$_3$/hexane (1:1) as the eluent. The title product 7 (386 mg, 83%) was obtained as a purple solid. $^1$H NMR (CDCl$_3$, 500 MHz): δ=8.59 (d, J=8.1 Hz, 2H), 8.29

(d, J=7.6 Hz, 2H), 7.74 (d, J=3.8 Hz, 2H), 7.60 (t, J=7.9 Hz, 2H), 7.35 (t, J=7.9 Hz, 2H), 7.22 (d, J=3.9 Hz, 2H), 6.95 (s, 2H), 2.82 (t, J=7.8 Hz, 4H), 1.66 (m, 4H), 1.40 (m, 4H), 1.22 (m, 16H), 0.84 (t, J=6.9 Hz, 6H). $^{13}$C NMR (CDCl$_3$, 500 MHz): δ=158.59, 143.83, 140.95, 140.30, 134.93, 132.97, 132.14, 132.08, 130.73, 129.43, 126.34, 125.76, 125.32, 125.02, 124.33, 121.95, 117.89, 111.32, 31.93, 30.5, 29.71, 29.69, 29.67, 29.62, 29.51, 29.49, 29.38, 22.70, 14.14. MS MALDI-TOF m/z 1130.24 (M$^+$, Calcd 1130.22).

Composition P1: A deoxygenated mixture of bromide 7 (150 mg, 132 μmol, 1.0 eq), trimethyltin monomer 8 (133 μmol, 1.0 eq), Pd$_2$(dba)$_3$ (3.64 mg, 3.97 μmol, 0.03 eq) and P(o-tol)$_3$ (4.83 mg, 15.9 μmol, 0.12 eq) in toluene (10 mL) was stirred for 16 h at 100° C. under N$_2$ atmosphere. 2-Bromothiophene was then injected into the mixture. Two hours later, 2-tributylstannyl thiophene was added and the reaction was stirred for another 2 hours. The reaction was quenched by precipitating the mixture in methanol. The precipitate collected from filtration was subjected to consecutive Soxhlet extractions with acetone, hexanes and chloroform, respectively. The chloroform fraction was condensed under reduced pressure and precipitated in acetone to give P1 (203 mg, 86%). The polymer collected from filtration was dried and stored in desiccator under vacuum. $^1$H NMR (C$_2$D$_2$Cl$_4$, 500 MHz, 130° C.): δ=8.56 (d, J=8.1 Hz, 2H), 8.21 (d, J=7.7 Hz, 2H), 7.70 (brs, 2H), 7.54 (m, 2H), 7.37 (m, 2H), 7.12 (m, 4H), 7.04 (brs, 2H), 4.18 (m, 4H), 2.86 (br s, 4H), 1.89 (m, 2H), 1.73 (m, 4H), 1.60 (m, 4H), 1.20 (m, 90H), 0.78 (m, 18H).

Composition P2: A deoxygenated mixture of bromide 7 (200 mg, 176 μmol, 1.0 eq), carbazole boronic acid ester 9 (176 μmol, 1.0 eq), K$_2$CO$_3$ (415 mg, 3 mmol, 1M in H$_2$O, 17 eq) and Pd(PPh$_3$)$_4$ (4.08 mg, 3.53 μmol, 0.02 eq) in toluene (10 mL) were vigorously stirred at 85° C. After 72 h, bromobenzene (4 μL, 0.03 mmol) was added into the reaction mixture. Three hours later, phenylboronic acid (4.3 mg, 0.03 mmol) was added and the reaction mixture was refluxed overnight to complete the end-capping reaction. The reaction mixture was washed with water and extracted with CHCl$_3$. Combined and concentrated CHCl$_3$ fraction was precipitated in methanol and the precipitate collected from filtration was subjected to consecutive Soxhlet extractions with acetone, hexanes and chloroform, respectively. The chloroform fraction was condensed under reduced pressure and purified by passing through a silica gel column with chloroform as eluent. The received solution was concentrated under reduced pressure and precipitated in acetone to give polymer P2 (203 mg, 82%). The polymer collected from filtration was dried and stored in desiccators under vacuum. $^1$H NMR (C$_2$D$_2$Cl$_4$, 500 MHz, 130° C.): δ=8.57 (d, J=7.5 Hz, 2H), 8.23 (d, J=8.1 Hz, 2H), 7.97 (d, J=8.1 Hz, 2H), 7.71 (s, 2H), 7.64 (s, 2H), 7.54 (t, J=7.2 Hz, 2H), 7.44 (d, J=8.1 Hz, 2H), 7.29 (m, 4H), 7.21 (s, 2H), 4.58 (m, 1H), 2.89 (br s, 4H), 2.27 (m, 2H), 2.02 (m, 2H), 1.76 (t, J=7.2 Hz, 4H), 1.45 (m, 6H), 1.20 (m, 54H), 0.78 (m, 12H).

What is claimed is:

1. A composition compound comprising of the formula:

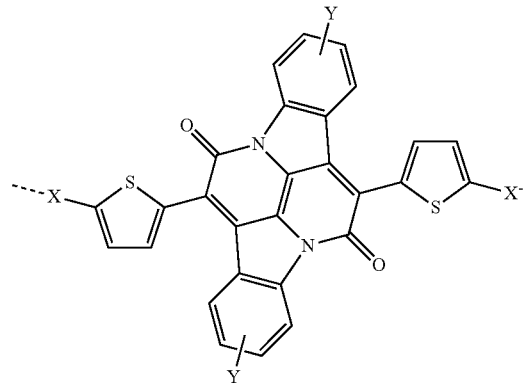

wherein x, y=F, Cl, Br, I,

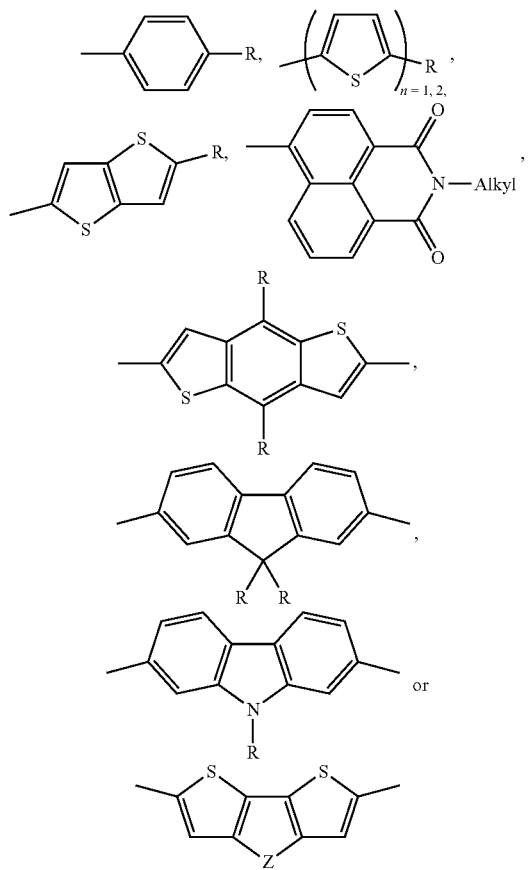

and R=-Alkyl, -OAlkyl, -SAlkyl, Z=—CR$_2$, NR, —SiR$_2$, —CR=CR—.

* * * * *